United States Patent [19]

Sullivan

[11] Patent Number: 4,519,386

[45] Date of Patent: May 28, 1985

[54] MOUTH SPLINT

[76] Inventor: Ashley H. Sullivan, 401 Gallaher View Rd., Apt. #46, Knoxville, Tenn. 37923

[21] Appl. No.: 518,617

[22] Filed: Jul. 29, 1983

[51] Int. Cl.³ .............................................. A61F 5/56
[52] U.S. Cl. ................... 128/136; 128/132 R; 128/359; 433/5; 433/10; 433/168; 433/170
[58] Field of Search ............... 128/136, 132 R, 359; 433/5, 6, 7, 8, 10, 11, 12, 17, 168, 169, 170, 172

[56] References Cited

U.S. PATENT DOCUMENTS

| | | | |
|---|---|---|---|
| 2,707,951 | 5/1955 | Shackelford | 128/136 |
| 3,089,487 | 5/1963 | Enicks et al. | 128/136 |
| 3,124,129 | 3/1964 | Grossberg | 128/136 |
| 3,496,936 | 3/1967 | Gores | 128/136 |
| 3,924,638 | 12/1975 | Mann | 128/136 X |

Primary Examiner—John D. Yasko
Assistant Examiner—Christa K. Scott
Attorney, Agent, or Firm—James C. Kesterson

[57] ABSTRACT

A concealed, resilient and flexible mouth splint for placing in the mouth of an individual around the upper maxillary posterior teeth to affect the tension of the masticator muscles of the individual is disclosed. The device comprises a right channel (22) and a left channel (24) for fitting over the left first molar and the right first molar, respectively. The top side (30A, 30B) of each channel member is molded to conform with the biting surface of the first molars, and each of the left and right channel members (22, 24) are molded to conform to the interior and exterior lateral surface of the first molar. This is a molded palate member (20) which arches between and integrally joins the two channel members, and which conforms with the roof of the mouth of an individual wearing this splint. The biting portion (28A, 28B) includes sufficient material such that the front upper teeth and the front lower teeth are maintained between two (2) and seven (7) millimeters. In addition, an airway is maintained through the mouth of the wearer even in intense physical activity. Accordingly to a preferred embodiment, the bottom side (32A, 32B) of the channel members is also molded to receive the irregularities of the biting surfaces of the opposing teeth of the lower jaw, and the mouth splint itself is made from a material having a Shore-A durometer hardness of between 30 and 70.

15 Claims, 4 Drawing Figures

MOUTH SPLINT

DESCRIPTION

Technical Field

This invention relates generally to devices clinched between the teeth, and more particularly to a mouth splint which can be used to help control the muscle tension of an individual wearer. The mouth splint may be used in a manner already suggested for accommodating stress and tension. In addition, the mouth splint has been found to be effective for controlling tension in masticatory jaw muscles for purposes of providing a competitive edge to the athlete or individual wearing the mouth splint. It also improves facial tone and provides relief of Temporomandibular joint pain and associated grinding of the teeth. Unlike previous or prior art devices, the mouth splint of this invention is not visible even when the wearer opens his/her mouth. Therefore, this device does not present a cosmetic or asthetic problem. Further, the mouth piece allows for substantially unaffected speech so that the wearer may keep the mouth splint in place and proceed about his or her business without providing any sound or visual cues to the presence of the mouth splint.

Background Art

As any one familiar with sporting equipment or activities will be aware, mouth pieces for protecting the teeth of people engaged in active and contact sports are well known. Certainly boxers have been using mouth pieces for many years and as will be appreciated by those skilled in the art, football players univerally use the mouth pieces during games or scrimmages. Examples of such protective mouth pieces are described in U.S. Pat. No. 3,124,129 issued to M. E. Grossberg, on Mar. 10, 1964, and U.S. Pat. No. 3,496,936 issued to K. W. Gores on Feb. 24, 1970. A closer review of these two patents, however, discloses that these appliances, or mouth pieces fit in the mouth between all of the teeth and have as a primary purpose protecting the teeth during physical activity or contact sports where impact forces may be received by the face or mouth area. However, as will also be appreciated by those skilled in the art, such mouth pieces are physically unattractive and prevent the user from speaking clearly and distinctly when in place. Therefore, as is well known, this type of mouth piece or protection device is continuously placed in the mouth and then removed during periods of non-contact. For example, the mouth piece is in place in the mouth of a boxer during each round but is removed in between rounds. Likewise for the football player, most mouth pieces are held in place only during the actual time the play is progressing and is not held in place during the huddle or between plays.

Similarly, there are mouth pieces or mouth protective devices typically designed for use by individuals or patients during extreme shock or trauma. For example, U.S. Pat. No. 2,708,931 issued to J. J. Freedland on May 24, 1955, discloses a device for use by shock therapy patients during the actual application of the shock therapy. This appliance is, of course, removed after the therapy is completed.

In addition to the well known mouth pieces or mouth protecting devices such as discussed above, which are for use by athletes during contact sports, it will be appreciated that recently it has been recognized that during periods of great tension the deleterious effect of such tension can be somewhat controlled by providing a device for an individual to clinch his teeth against. For example, U.S. Pat. No. 3,924,638 issued to G. E. Mann on Dec. 9, 1975, discloses two embodiments of such a tension relieving mouth appliance. Unfortunately, as was the case for the mouth pieces for contact sports and the like, these tension relieving mouth appliances are also readily visible when in place, and usually result in slurred or unclear speech by the wearer. Consequently, as would be expected, such devices cannot be worn all the time, and certainly cannot be worn by an individual under great stress at a formal meeting if the individual would be required to be very coherent, clear, emphatic, and percise in his speech. Thus, it will be appreciated that at the very time an individual under formal stress may most need an appliance, the prior art devices are not suitable for him to wear.

In addition, recent studies indicated that controlled stress of selected muscles, such as the masticator muscles in the jaw have a desirable cumulative effect on an athlete or other individual in a competitive situation. That is, if particular selected muscles of the face can be brought to a selected tension or tonus, this tonus can affect other muscles of the body by increasing their tone and readiness for activity such that the athlete or wearer may achieve a competitive edge for a period of time. To this date, the applicant is not aware of any devices or mouth pieces particularly designed to provide such selected tension, and help increase the competitive edge of an individual athlete or wearer.

Therefore, it is an object of the present invention to provide a mouth splint or device suitable for helping control tension of the wearer which is easy and simple to use.

It is still another object of the present invention to provide a mouth splint that is not visible to persons observing the wearer.

It is yet another object of the present invention to provide a mouth device for controlling tension that may be continuously worn with little or no detrimental effect on the clarity of speech of the wearer.

Still another object of the present invention is to provide a device for controlling tension that may both help to relieve tension, and in selected situations provide increased tension or tonus to muscles to provide a competitive edge.

Another object of the present invention is to provide a mouth splint for relieving Temporomandibular Joint Pain, and the associated grinding of the teeth that might have been caused by increased muscle tonus.

Yet another object of the present invention is to provide a device for increasing the tonus of facial muscles.

Disclosure of the Invention

Other objects and advantages will in part be obvious, and will in part appear hereinafter, and will be accomplished by the present invention which discloses a concealed, resilient and flexible mouth splint for placing in the mouth of an individual around the upper maxillary posterior teeth to effect the tension of the masticator muscles of the individual. The mouth splint comprises a left channel shaped member and a right channel shaped member, each of which are made of a resilient and flexible non-toxic material. Each of the left and right channels fit over at least the first molar on the left and right side of the upper jaw respectively. Also, each of the left and right channels have a biting portion with a top and bottom side. The top side is molded to conform with the biting surface of the first molar. Further, each of the left and right channel members have an interior wall integrally joined with the biting portion and molded to conform with the inside lateral surface of the first molars and similarily each channel has an exterior wall integrally joined with the biting portion and molded to conform with the outside lateral surface of the teeth. The palate member is also made of the same resilient material as the channel members, and arches between and integrally joins the inner walls of the left and right channel members. The palate member is of a thin cross-section, and is molded to conform with the roof of the mouth of the individual wearing the device. The left and right channel members and the palate member cooperate to provide the mouth splint which conforms with the roof of the mouth and conforms and then encloses the left and right first molar of the individual. The biting portion of the left and right channel members include a sufficient amount of the flexible and resilient material to maintain the top and bottom sides of the biting portion spaced a selected distance such that the lower front teeth of a person wearing the device is maintained between two (2) and seven (7) millimeters, and preferably between four (4) and six (6) millimeters from the upper teeth. In a preferred embodiment, the left and right channel members also enclose and conform to at least a portion of the second pre molars which are in front of the first molars and the second molars which are to the rear of the first molars. Further, in a preferred embodiment, the device is made of a resilient material having a Shore-A value of between 30 and 70.

BRIEF DESCRIPTION OF THE DRAWINGS

The above mentioned features of the present invention will be more clearly understood from the consideration of the following description in connection with the accompanying drawings in which.

BEST MODE FOR CARRYING OUT THE INVENTION

Figure 1:
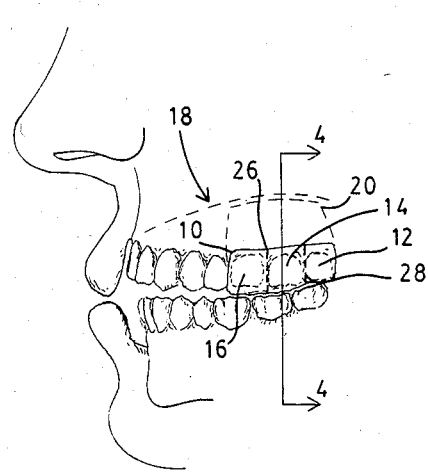
FIG. 1 is a side view of the mouth splint of this invention in place in a wearer's mouth and showing its location with respect to the teeth.

The mouth splint or appliance of this invention allows the athlete, dancer or other user to develop a tonus to the jaw or masticator muscles by clinching the teeth firmly against the mouth splint as the athlete or dancer concentrates and anticipates the required physical activity or competitive effort. At the same time, as will be clearly seen in the discussion hereinafter, the mouth splint of this invention maintains a clear or patent air way which is more than adequate for the increased respiratory requirements of the physical activity. In addition, in certain activities such as dancing, certain gymnastic events, etc., where beauty and form are involved, the appliance is not visible, and therefore is aesthestically appealing to the wearer.

The increased muscle tonus of the masticator muscles it is believed, will in turn provide an impulse or message which will be transferred to the brain and then to the rest of the muscles of the body by means of the branches of the Fifth Cranial Nerve (Trigeminal). Thus, an increase in tonus of the masticator muscles effect an increase in tonus in many other skeletal muscles throughout the body. Particularly, it is noted that the Trigeminal nerve is divided into three major divisions (Opthalmic, Maxillary and Mandibular) and that the Mandibular Division carries motor innervation as well as sensory inputs from the teeth and gums. That is, the Mandibular Nerve provides pathways for both sensory input to the teeth and gums and motor input to the muscles of mastication. Closer studies of the Mandibular nerve, however, reveal that the sensory input for the masticator muscles is not readily seen to be carried or depicted by any particular nerve tract. It is well known, of course, that the masticator muscles have many sensory inputs including proprioception (this is pressure and kinesthesis). Of course, the teeth themselves and the gums or peridontium areas also help to finely tune the masticator muscles in their various movements. But, it is this vast network of sensory fibers, which includes these various nerves and which are associated with the teeth, which is believed can transfer intense concentration. Even though it is recognized that there may be a vast network of sensory inputs with respect to the teeth, understanding just how an impulse is relayed from the masticator muscles is difficult. However, we do know that there are sensory fibers located in the stretch receptors of the masticator muscles. Thus, sensory inputs from the masticator muscles concerning muscle tonus are relayed from these muscles to the Mesencphalic Nucleus in the brain. From the Mesenciphalic Nucleus these sensory inputs are forwarded to the Cerebellum which is the primary area of the brain responsible for controlling muscle tonus. After receiving this stimuli, the Cerebellum is free to adjust the overall tonus throughout the skeletal muscles of the body. As is known by those skilled in the art, the Cerebellum assimilates all of the information from all of the stretch receptors all over the body and establishes an overall tonus of the bodily muscles in accordance with the information it has obtained from the entire quantum of stretch receptors.

Therefore, it would seem that if the overall information that the Cerebellum obtains is changed or altered, then the overall tonus of the entire body could also be altered. It is because of this cause-effect that the runner in anticipation of a race stretches, takes short sprints, and even consciously gnashes his teeth prior to the competition. These activities are believed to increase the tonus of all of the muscles of the runner's body thereby better preparing the runner for the race. Therefore, it would only seem feasible that in a similar manner, use of the mouth splint of this invention will increase the tonus in one part of the body, namely the masticator muscles, and this increase will cause an associated reflex or response in the other skeletal muscles of the body. This is not simply a muscle contraction, but is in fact an increase in the muscle tonus or readiness of the muscles for response. Thus, by an extrinsic means such as the mouth splint it is believed that one can establish an increase tonus or readiness for response of all the muscles throughout the body.

In addition to the establishment of increased tonus in all the skeleton muscles, the mouth splint of the present invention also provides a means to focus the athlete's complete concentration. Just as the absorbed reader or the movie goer might clinch his fist or gnash his teeth as he concentrates on the story or play, just as the cowboy was given a bullet to bite to convey his attention away from painful surgery, likewise the athlete needs to direct his attention to one central focus spot. However, with present mouth pieces and mouth protectors, the athlete cannot bear down on one spot and gnash his teeth together since with such presently available devices, a patent or clear air way cannot be maintained sufficient to allow the required respiration needed for the athletic event. The present invention on the other hand allows this concentrated clinching of the teeth and peak muscle activity while maintaining an air way sufficient to provide air even in the most intense athletic competition.

In addition to the control of muscle tone to aid in competative situations, the mouth splint of this invention is also believed to be effective for relieving Temporomandibular Joint Pain related to increased muscle tonus, and for increasing the tone of facial muscles. For example, understanding the physiology of the masticator muscles and their relationship to the jaw bone socket or Glenoid Fossa, a technique for treating abnormalities of this area was suggested to the applicant. The primary muscles of mastication are the Lateral Pterygoid, Medial Pterygoid, Temporalis, and Masseter muscles. Ordinarily, these muscles function synchronously and are unnoticed. However, if one of these muscles experiences a spasm, there is immediately concern. Since the smallest and most overused muscles should be the first to portray signs of fatigue and cramping, it follows that the Lateral Pterygoid (involded in protrusion) and Temporalis muscles (closing movement) would experience the most problems which, in fact, is the case.

Considering the contractile process of a muscle suggests that muscles respond best when they are at their normal resting length, and indeed, current studies indicate the strongest contractile ability of a muscle is when the muscle is at its fully stretched resting length. That is, when the Actin filaments completely overlap the Myosin Filiments and are just beginning to overlap each other. This length allows the contractile fibers to have their greatest potential to form cross bridges and produce contraction. Therefore, the best realm for a muscle to function is believed to be neither the fully stretched or fully contracted state, but at a length that allows harmonious function with minimal strain on the muscles and the most interaction of the elements of contraction.

Comparing the muscle physiology of the face with that of other skeletal muscles suggested to the applicant a method of treating facial muscles. Every skeletal muscle has a finite amount of potential energy which is exhausted when muscle fatigue occurs. Thus, when this potential energy is tapped and dissipated, the muscle is forced to accept a more relaxed tonus, since there is no longer energy available to maintain a contraction. For example, after a stimulating workout the muscles of a runner are more relaxed and temporarily depleted of their ready store of energy. Therefore, it follows that with long periods of disuse, the facial muscles develop a tonus in anticipation of use as do muscles in the rest of the body. However, in most cases the masticator muscles are not exhausted by either diet or exercise. Unfortunately, this stored energy potential remains and the masticator muscles maintain an elevated level of tonus in anticipation of their use. Therefore, since the muscles of mastication do not routinely release this potential energy, a person will often develop other methods of release. For example, patients consciously grind their teeth in an intense situation, employing the excess energy in a deleterious direction. Similarly, at night, many patients unconsciously viciously brux their teeth to exhaust this stored energy. As discussed heretofore, a muscle performs best at its optimally stretched resting length, and the facial muscles are skeletal muscles that also require such use. The mouth splint of this invention facilitates the use of these masticator muscles in their most comfortable state, such that some of the vast storehouse of energy and tension is exhausted. After using or exercising the facial muscles with the mouth spling of this invention, they feel more relaxed and the patient perceives he has gained space between his teeth. This means there is less tendency for the teeth to touch, and this realization reduces the feeling of being "on edge". Thus, like other muscles, the facial muscles benefit by being employed.

As discussed heretofore, the knowledge of muscle function may be related to Temporomandibular Joint Pain, and associated grinding of teeth. As will be appreciated by those skilled in the art, the masticator muscles rule the position of the teeth, and since the condyles are part of the mandible, they are also subject to the control of the muscles. Therefore, whether or not the facial muscles are in a relaxed comfortable positon that allows the condyles to be properly seated in the Glenoid Fossa or in a less optimal arrangement that allows potential pathology or problems to develop depends on the masticator muscles. To this end, the resilient quality of the mouth splint of this invention provides smooth, loose occlusion of the teeth, thereby allowing muscular function and letting the teeth occlude where they feel comfortable. Also, the mouth splint of this invention will not allow the condyles to seat as far in a posteriosuperior direction, so there are less potential problems of the Temporomandibular joint in that the Tempormandibular joint is allowed an unrestricted neurovascular supply while the pressure on the condyle is lessened. Thus a static position of the Temporomandibular joint is prevented and the facial muscles have freedom of movement, such that areas that were previously continually assaulted, are given a rest.

Thus, it is seen that by using the mouth splint of this invention in daily exercise, the facial muscles can be toned, in the same manner as exercise tones and relaxes the rest of our bodies. In spite of all the recent concern about exercising and developing our bodies, the care and relaxation of the facial muscles has been largely overlooked. Persons often look at themselves and wonder why their faces age more rapidly than the rest of our bodies and show the lines of tension sooner. Yet, few, if any, exercise programs consciously exercise or stretch the muscles of the face.

Figure 2:
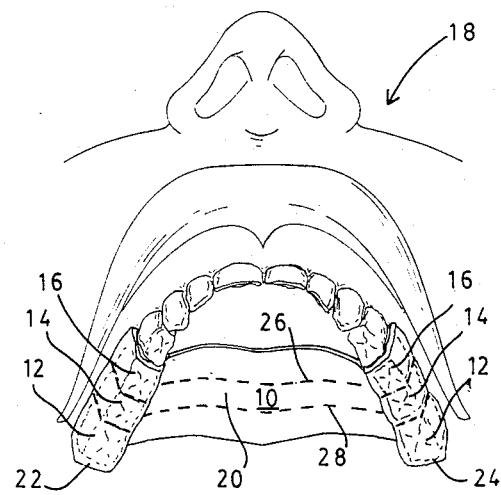
FIG. 2 is a view of the mouth splint in place looking into the mouth of the wearer toward the upper jaw.

Referring now to FIGS. 1 and 2, there are shown a side view and bottom view, respectively, of the device 10 in place which enclose the upper maxillary posterior teeth 12, 14 and 16 in the mouth of an individual 18. Also as shown in FIG. 2, and by dotted lines in FIG. 1, and as will be discussed in detail hereinafter, there is a palate or arching member 20 which joins those portions of the device 10 which encloses the teeth 12, 14 and 16, as well as the same teeth on the other side of individual's 18 jaw. The arching member 20 is more readily seen in the view of FIG. 2 which shows the palate member 20 connecting and joining the two channel members 22 and 24 enclosing the teeth of the individual. In the embodiment shown, the channel members 22 and 24 enclose and protect the three rear most teeth 12, 14 and 16 of the upper jaw. However, as is indicated by dotted lines 26 and 28, an alternate embodiment of the invention may be made to only enclose the first molars 14.

Figure 3:
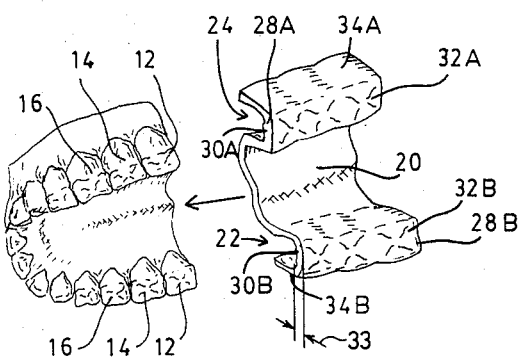
FIG. 3 is a prospective view of the mouth splint and the upper teeth of a wearer.

Referring now to FIG. 3, there is shown a prospective view of the mouth splint of this invention as it would appear when not in place in an individual's mouth. As shown and discussed above, the mouth splint includes a left channel member 24 and a right channel member 22 which in the preferred embodiment enclose and are molded to conform with the contours of the second molars, first molars, and second pre molars on each side of the individual's upper jaw. Futher, the palate member 20 is formed of the same material and is molded as an integral piece with the channel members 22 and 24 and is also molded to conform with the palate or roof of the mouth of the individual destined to wear the device. As shown, each of the channels 22 and 24, have a biting portion 28A and 28B with a top surface 30A and 30B, and a bottom surface 32A and 32B.

To achieve the desired increase tonus of the muscular system of the individual, it has been found that the upper and lower front teeth should be opened with respect to each other approximately four (4) or six (6) millimeters, even when the teeth are clinched against the splint. Thus, since the opening between the upper and lower front teeth is usually greater than the space between the upper and lower molars by a ratio of about 3:1, it will be appreciated that the biting surfaces of upper molars 14A and 14B should be separated by a space of between about 1.33 and 2.0 millimeters. Further, as an outside limit for most patients, it is believed that the distance between the front teeth must be at least two (2) millimeters and not greater than seven (7) millimeters with a corresponding outside limit of between 0.67 and 2.33 millimeters between the upper and lower molars. Since the device will likely be used more often by patients having most of their back teeth, the two (2) to seven (7) millimeter spacing should be correct for such patients. It will be appreciated, however, that for patients who have lost their back teeth, or have unusually large or abnormal bone structure, even larger distances could be required. As is known by those skilled in the art, the condyle bone or jaw bone rotates in its socket (Glenoid Fossa) when the mouth is open to no more than about four (4) to six (6) millimeters, but any further opening of the mouth requires that the condyle bone slide down the Glenoid Fossa to allow further opening of the jaw. Thus, it is seen that to achieve the desired results of this invention, it is necessary that sufficient material, of a resilient and flexible type, be provided such that when the device is in place in a normal patient, the upper and lower front teeth will be maintained the desired four (4) to six (6) millimeters spacing. It will further be appreciated that if the device is to fit securely in the mouth and remain in place even when the mouth is opened widely, the channels 22 and 24 should be molded around the teeth 12, 14, and 16, for a close fit and that the palate member 20 should also be molded to follow the contours of the roof of the mouth. In addition, in a preferred embodiment, it is believed that the bottom surface 32A and 32B of each left and right channel is preferrably molded with impressions to accept the cusps or irregularities of the lower biting teeth. Thus, when the teeth are clinched together, the biting surface of the upper teeth fit the molded top side 30A and 30B, and the bottom side 32A and 32B is molded to receive the irregularities of the lower teeth.

Figure 4:
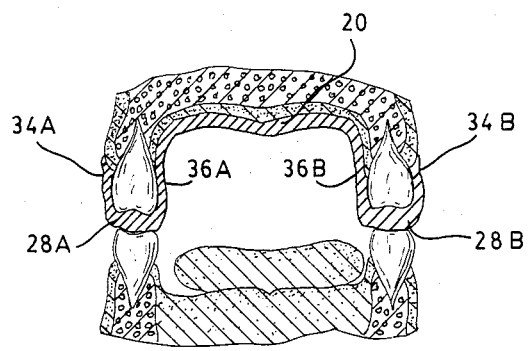
FIG. 4 is a cross-sectional view of the mouth splint of this invention taken along lines 4—4 of either FIG. 1 or 3.

FIG. 4 shows a cross-sectional view of the mouth splint of this invention and also shows how the exterior walls 34A and 34B are molded to the outside lateral surfaces of the teeth and the interior walls 36A and 36B are molded to the inside leteral surfaces of the teeth. Likewise, it is again seen that the top sides 30A and 30B are molded to receive the irregularities of the upper teeth and the bottom side 32A and 32B are molded to receive the biting surfaces of the teeth of the lower jaw. Likewise, the palate member 20 is molded to follow the contours of the roof of the mouth or the palate of the individual wearing the device.

It should also be understood, that the material from which this device is made is a resilient and flexible material and is not a hard denture material as are many protection type mouth pieces. A very effective material for use of this device is Ortho-acrylic material available from Henry Shein, Inc. of Port Washington, N.Y. Other theromosetting materials well known as dental materials may also be used, of course, so long as the durometer hardness, Shore-A value, is between about 30 to 70.

Thus, although the present invention has been described with respect to specific designs and embodiments for providing a mouth splint for helping to control and affect the tonus of the masticator muscles, it is not intended that such specific references be considered as limitations upon the scope of this invention except in so far as is set forth in the following claims.

I claim:
1. A concealed resilient and flexible mouth splint for placing in the mouth of an individual around the upper maxillary posterior teeth to effect the tonus of the masticator muscles of the individual comprising:
   a left channel shaped member and a right channel shaped member made of a resilient and flexible non-toxic material, said left and right channel members for fitting over the left first molar and the right first molar, respectively, each of said left and right channel members having a biting member with a top and bottom side, said top side being molded to conform with the biting surface of said first molars, each of said left and right channel members having an inner wall integrally joined with said biting portion and molded to conform to the interior lateral surface of said first molars, and each of said left and right channel members having an outer wall intrigally joined with said biting portion and molded to conform to the exterior lateral surface of said first molar; and
   a palate member made of said resilient and flexible material arching between and integrally joined with said inner wall of said left channel member and said inner wall of said right channel member, said palate member being molded to conform with the roof of the mouth of an individual wearing said mouth splint, said biting portion of said left and right channel member including a sufficient amount of said flexible and resilient material to maintain said top and bottom sides of said biting portion spaced a selected distance by said biting portion of said left and right channel members, and such that an air way is maintained through the mouth of the wearer.

2. The mouth splint of claim 1, wherein said sufficient resilient material will provide a spacing of between 0.67 and 2.33 millimeters between the biting surfaces of the opposing lower teeth and the biting surface of said left and right upper first molars.

3. The mouth splint of claim 2, wherein said left and right channel members extend anteriorly and posteriorly beyond said first molars and are molded to conform to and enclose at least a portion of an adjacent second molar and an adjacent second pre-molar.

4. The mouth splint of claim 2, wherein the bottom side of said biting portion of said channel member is molded to conform with the biting surface of said opposing teeth on the lower jaw of said individual wearing said mouth splint.

5. The mouth splint of claim 3, wherein the bottom side of said biting portion of said channel member is molded to conform with the biting surface of said opposing teeth of the lower jaw of an individual wearing said mouth splint.

6. The mouth splint of claim 2, wherein said sufficient resilient material will provide a spacing of between 1.33 and 2.00 millimeters between the biting surface of said upper first molars and the biting surface of opposing teeth in the lower jaw of an individual wearing said mouth splint.

7. The mouth splint of claim 3, wherein said sufficient resilient material will provide a spacing of between 1.33 and 2.00 millimeters between the biting surface of said upper first molars and the biting surface of opposing teeth in the lower jaw of said individual wearing said mouth splint.

8. The mouth splint of claim 4, whrein said sufficient resilient material will provide a spacing of between 1.33 and 2.00 millimeters between the biting surface of said upper first molars and the biting surface of opposing teeth in the lower jaw of said individual wearing said mouth splint.

9. The mouth splint of claim 5, wherein said sufficient resilient material will provide a spacing of between 1.33 and 2.00 millimeters between the biting surface of said upper first molars and the biting surface of opposing teeth in the lower jaw of said individual wearing said mouth splint.

10. The mouth splint of claim 1, wherein said resilient material has a Shore-A durometer hardness of between 30 to 70.

11. The mouth splint of claim 2, wherein said resilient material has a Shore-A durometer hardness of between 30 and 70.

12. The mouth splint of claim 3, wherein said resilient material has a Shore-A durometer hardness of between 30 and 70.

13. The mouth splint of claim 4, wherein said resilient material has a Shore-A durometer hardness of between 30 and 70.

14. The mouth splint of claim 5, wherein said resilient material has a Shore-A durometer hardness of between 30 and 70.

15. A concealed resilient and flexible mouth splint for placing in the mouth of an individual around the upper molars to effect the tonus of the masticator muscles of the individual comprising:

a left channel shaped member and a right channel shaped member made of a resilient and flexible non-toxic material having a durometer Shore-A value of between 30 and 70, said left and right channel members for fitting over the left and right second molars, first molars and second pre-molars, respectively, each of said left and right channel members having a biting member with a top and bottom side, said top side being molded to conform with the biting surface of said second molars, first molars and second pre-molars, and said bottom side molded to conform to the cusps of the opposing lower teeth. each of said left and right channel members having an inner wall integrally joined with said biting portion and molded to conform to the interior lateral surface of said second molars, first molars, and second pre-molars, and each of said left and right channel members having an outer wall intrigally joined with said biting portion and molded to conform to the exterior lateral surface of said second molars, first molars and second pre-molars; and a palate member made of said resilient and flexible material arching between and integrally joined with said inner wall of said left channel member and said inner wall of said right channel member, said palate member being molded to conform with the roof of the mouth of an individual wearing said mouth splint, said biting portion of said left and right channel member including a sufficient amount of said flexible and resilient material to maintain said top and bottom sides spaced a selected distance such that the opposing lower teeth of such an individual are maintained between 1.33 and 2.00 millimeters from the biting surface of said second molars, first molars and second pre-molars, and such that an air way is maintained through the mouth of the individual.

* * * * *